United States Patent
Dekeyser et al.

Patent Number: 5,677,301
Date of Patent: Oct. 14, 1997

[54] PESTICIDAL OXADIAZINES

[75] Inventors: Mark Achiel Dekeyser, Waterloo, Canada; Paul Thomas McDonald, Middlebury, Conn.

[73] Assignees: Uniroyal Chemical Company, Inc., Middlebury, Conn.; Uniroyal Chemical Ltd., Elmira, Canada

[21] Appl. No.: 636,295

[22] Filed: Apr. 23, 1996

Related U.S. Application Data

[63] Continuation-in-part of Ser. No. 241,211, May 11, 1995, Pat. No. 5,536,720, which is a continuation-in-part of Ser. No. 942,705, Sep. 9, 1992, abandoned.

[51] Int. Cl.$^6$ .................... C07D 273/04; A01N 43/88
[52] U.S. Cl. .................... 514/229.2; 544/66
[58] Field of Search .................... 544/66; 514/229.2

[56] References Cited

PUBLICATIONS

Ishidate et al, Chem. Pharm. Bull, vol. 7, 391 (1959).

*Primary Examiner*—John M. Ford
*Attorney, Agent, or Firm*—Daniel Reitenbach

[57] ABSTRACT

Compounds of the formula

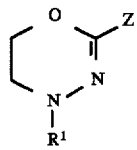

wherein:

Z is a)

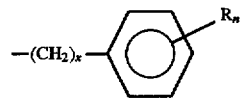

wherein x is an integer from 0 to 4, n is an integer from 0 to 5 and R is defined below; or b)

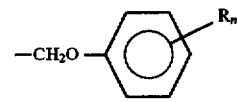

wherein n is an integer from 0 to 5 and R is defined below;

R is selected from the group consisting of: hydrogen; $C_1$–$C_4$ alkyl; $C_1$–$C_4$ alkoxy; halogen; nitro; phenyl; cyano; phenoxy; benzyloxy; benzyl; $C_1$–$C_4$ dialkylamino; $C_1$–$C_4$ alkylthio; or $C_1$–$C_4$ haloalkyl; and $R^1$ is a $C_1$–$C_4$ haloalkyl other than a chloroalkyl, or a group of the formula

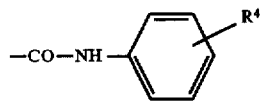

wherein $R^4$ is halogen, $C_1$–$C_4$ haloalkyl or $C_1$–$C_4$ haloalkoxy;

or physiologically acceptable salts thereof. These compounds exhibit insecticidal and acaricidal activity.

9 Claims, No Drawings

PESTICIDAL OXADIAZINES

This is a continuation-in-part of U.S. application Ser. No. 08/241,211, filed on May 11, 1995, now U.S. Pat. No. 5,536,720 continuation-in-part of U.S. application Ser. No. 07/942,705, filed on Sep. 9, 1992, now abandoned.

FIELD OF THE INVENTION

This invention is directed to substituted oxadiazines, which compounds exhibit unexpectedly desirable activity as pesticides, including as insecticides and acaricides. In other aspects, this invention is directed to pesticidal compositions comprising such compounds as well as to methods of controlling pests employing such compounds and/or compositions.

The destruction by acarids and insects presents a serious problem to agriculture. A wide variety of field crops are in need of protection from acarids and/or insects including such valuable crops as soybeans, corn, peanuts, cotton, alfalfa and tobacco. In addition, vegetables such as tomatoes, potatoes, peas, sugarbeet, carrots and the like, as well as fruits, nuts, ornamentals and seed bed crops such as apples, peaches, citrus fruit, almonds and grapes may also require protection from the ravages of such pests.

DESCRIPTION OF RELATED ART

J. Med. Chem, 1966, 753–758 refers to various 2-substituted 4H-1,3,4-oxadiazines said to have anticonvulsant activity in mice. U.S. Pat. No. 3,420,826 refers to certain 2,4,6-substituted 4H-1,3,4-oxadiazines, said to have utility as sedatives, anticonvulsants, and as pesticides, specifically against nematodes, plants, and fungi. U.S. Pat. No. 3,420,825 refers to methods for producing those compounds.

SUMMARY OF THE INVENTION

In one aspect, the present invention is directed to compounds having the formula:

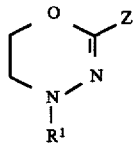

wherein:
Z is
a)

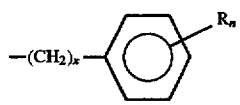

wherein x is an integer from 0 to 4, n is an integer from 0 to 5 and R is defined below; or b)

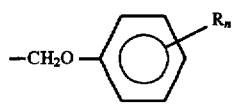

wherein n is an integer from 0 to 5 and R is defined below;

R is selected from the group consisting of: hydrogen; $C_1$–$C_4$ alkyl; $C_1$–$C_4$ alkoxy; halogen; nitro; phenyl; cyano; phenoxy; benzyloxy; benzyl; $C_1$–$C_4$ dialkylamino; $C_1$–$C_4$ alkylthio; or $C_1$–$C_4$ haloalkyl; and $R^1$ is a $C_1$–$C_4$ haloalkyl other than a chloroalkyl, preferably a $C_1$–$C_4$ fluoroalkyl, or a group of the formula

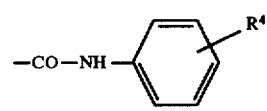

wherein $R^4$ is hydrogen, halogen, $C_1$–$C_4$ haloalkyl or $C_1$–$C_4$ haloalkoxy, preferably a group of the formula

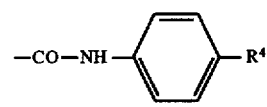

wherein $R^4$ is halogen, $C_1$–$C_4$ fluoroalkyl or $C_1$–$C_4$ fluroalkoxy, more preferably —Cl, —$CF_3$ or —$OCF_3$; and physiologically acceptable salts thereof.

The compositions of this invention are comprised of (A) one or more compounds having the structure of formula I above, and (B) a suitable carrier. Such suitable carriers may be solid or liquid in nature. The compounds and compositions of the present invention exhibit pesticidal activity, especially against insects and acarids.

DETAILED DESCRIPTION OF THE INVENTION

The compounds of this invention can be prepared by reacting a hydrazide of formula (III) below

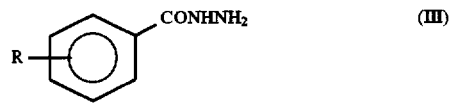

where R has the meanings described above, with 1-bromo-2-fluoroethane in the presence of a base. Such bases include alkali metal hydroxides. Preferred bases include sodium or potassium hydroxide.

The compositions of the present invention may be prepared by formulating one or more compounds of the present invention with a suitable carrier, such as a liquid or solid carrier.

Suitable liquid carriers may be comprised of water, alcohols, ketones, phenols, toluene and xylenes. In such formulations, additives conventionally employed in the art may be utilized, such as one or more surface active agents and/or inert diluents, to facilitate handling and application of the resulting pesticide composition.

Alternatively, the pesticidal compounds may be applied in liquid or sprays when utilized in a liquid carrier, such as in a solution comprising a compatible solvent such as acetone, benzene, toluene or kerosene, or as dispersed in a suitable non-solvent medium such as water.

The pesticidal compositions may alternatively comprise solid carriers taking the form of dusts, granules, wettable powders, pastes, aerosols, emulsions, emulsifiable concentrates, and water-soluble solids. For example, the pesticidal compounds of this invention may be applied as dusts when admixed with or absorbed onto powdered solid carriers, such as mineral silicates, e.g., mica, talc, pyrophyllite and clays, together with a surface-active dispersing agent so that a wettable powder is obtained which then is applied directly to the loci to be treated. Alternatively, the powdered solid carrier containing the compound admixed therewith may be dispersed in water to form a suspension for application in such form.

Granular formulations of the compounds are preferred for field treatment and are suitable for application by broadcasting, side dressing, soil incorporation or seed treatment, and are suitably prepared using a granular or pellitized form of carrier such as granular clays, vermiculite, charcoal or corn cobs. The pesticide is dissolved in a solvent and sprayed onto an inert mineral carrier such as attapulgite granules (10–100 mesh), and the solvent is then evaporated. Such granular compositions may contain from 2–25% pesticide based on carrier plus pesticide, with 3–15% being preferred. In addition, the pesticide may also be incorporated into a polymeric carrier such as polyethylene, polypropylene, butadiene-styrene, styrene-acrylonitrile resins, polyamides, poly(vinyl acetates) and the like. When encapsulated, the pesticide may advantageously be released over an even longer time period, extending its effectiveness further than when used in non-encapsulated form.

Another method of application to loci to be treated is aerosol treatment, for which the compound may be dissolved in an aerosol carrier which is a liquid under pressure but which is a gas at ordinary temperature (e.g., 20° C.) and atmospheric pressure. Aerosol formulations may also be prepared by first dissolving the compound in a less volatile solvent and then admixing the resulting solution with a highly volatile liquid aerosol carrier.

For pesticidal treatment of plants (such term including plant parts), the compounds of the invention preferably are applied in aqueous emulsions containing a surface-active dispersing agent which may be non-ionic, cationic or anionic. Suitable surface-active agents are well known in the art, and include those disclosed in U.S. Pat. No. 2,547,724 (columns 3 and 4). The compounds of the invention may be mixed with such surface-active dispersing agents, with or without an organic solvent, as concentrates for the subsequent addition of water to yield aqueous suspensions of the compounds at desired concentration levels.

In addition, the compounds may be employed with carriers which themselves are pesticidally active, such as insecticides, acaricides, fungicides or bactericides.

It will be understood that the amount of the pesticidally active compound in a given formulation will depend upon the specific pest to be combatted, as well as upon the specific chemical composition and formulation of the compound being employed, the method of applying the compound/formulation and the locus of treatment so that the pesticidally effective amount of the compound may vary widely. Generally, however, concentrations of the compound as the active ingredient in pesticidally effective formulations may range from about 0.1 to about 95 percent by weight. Spray dilutions may be as low as a few parts per million, while at the opposite extreme, full strength concentrates of the compound may be usefully applied by ultra low volume techniques. When plants constitute the loci of treatment, concentration per unit area may range between about 0.01 and about 50 pounds per acre, with concentrations of between about 0.1 and about 10 pounds per acre preferably being employed for crops such as corn, tobacco, rice and the like.

To combat pests, sprays of the compounds may be applied to any suitable locus, such as to the pests directly and/or to plants upon which they feed or nest. The pesticidally active formulations may also be applied to the soil or other medium in which the pests are present. Harmful insects and acarids attack a wide variety of plants, including both ornamental and agricultural plants and inflict damage by consuming roots and/or foliage, withdrawing vital juices from the plants, secreting toxins and often by transmitting diseases. The compounds of the present invention may be advantageously utilized to minimize or prevent such damage. The specific methods of application, as well as the selection and concentration of these compounds will of course vary depending upon such circumstances as geographic area, climate, topography, plant tolerance, etc. For specific circumstances, one skilled in the art may readily determine the proper compound, concentration and method of application by routine experimentation.

The compounds of the invention are particularly useful as insecticides and acaricides for foliar application. The compounds are particularly effective for controlling insects, such as tobacco budworm and mites, such as spider mites and rust mites.

The following examples are given merely to illustrate the scope of the present invention. The invention herein is not intended to be limited to the actual examples provided.

EXAMPLE 1

Preparation of 2-(4-Bromophenyl)-4H-1,3,4-Oxadiazine (Compound No. 16)

A solution of 2.9 g (0.07 mole) sodium hydroxide dissolved in 10 ml of water was added dropwise at room temperature to a mixture of 6.5 g (0.03 mole) 4-bromobenzoic hydrazide and 4.0 g (0.03 mole) 1-bromo-2-fluoroethane in 25 ml of ethanol. The resulting solution was refluxed for two and one-half hours. The mixture was cooled to room temperature, diluted with 150 ml of water and extracted several times with ether (100 ml). After separation and drying over anhydrous sodium sulfate, the solution was filtered and evaporated under reduced pressure leaving 4.6 grams of an oil (63.6% yield), which was purified by distillation. The product was characterized by IR and NMR spectroscopy.

EXAMPLE 1A

Prepartation of 2-(4-bromophenyl)-5,6-dihydro-N-[(4-trifluoromethyl)phenyl]-4H-1,3,4-oxadiazine-4-carbamide (Compound 70)

To 1 gm of 2-(4-bromophenyl)-5,6-dihydro-4H-1,3,4-oxadiazine dissolved in 40 ml of acetonitrile, was added, with stirring, 2 drops of triethylamine followed by 1 gm of 4-(trifluoromethyl)phenyl isocyanate and stirred for 1 hour at room temperature. The solvent was then evaporated under reduced pressure and the resulting solid was washed with hexane and air-dried, producing 1.0 gm of 2-(4-bromophenyl)-5,6-dihydro-N-[(4-trifluoromethyl)phenyl]-4H-1,3,4-oxadiazine-4-carbamide, mp 146°–148° C. (50% yield).

Additional compounds were prepared in accordance with the above procedures. These compounds and their acaricidal and insecticidal activity are summarized in Tables I and II. The NMR data are summarized in Table III.

TABLE I

| CMPD # | R | X | R¹ | MI | MIOVL | RPH | TB | TBOV |
|---|---|---|---|---|---|---|---|---|
| 1 | 2-F | — | H | 0 | 70(0) | 50 | 40 | 100 |
| 2 | H | $CH_2$ | H | 0 | 100(0) | 50 | 20 | 0 |
| 3 | H | — | $CONHC_6H_4Cl$ | 0 | 100(0) | 30 | 0 | 0 |
| 4 | $4-CH_3$ | — | $CH_3$ | 0 | 40(0) | 86 | 0 | 0 |
| 5 | $4-CH_3O$ | — | H | 0 | 0 | 100 | 80 | 100 |
| 6 | $4-CH_3O$ | — | $CONHC_6H_4Cl$ | 0 | 70(L) | 100 | 46 | 100 |
| 7 | 4-F | — | H | 100 | 50(L) | 90 | 80 | 89 |
| 8 | 2,4-Cl | $CH_2O$ | H | 0 | 0 | 100 | 40 | 99 |
| 9 | 2,4-Cl | $CH_2O$ | $CONHC_6H_5$ | 0 | 70(L) | 100 | 0 | 56 |
| 10 | 2,5-Cl | — | H | 70 | 100(0) | 100 | 80 | 100 |
| 11 | 4-Cl | — | H | 0 | 70(0) | 50 | 80 | 100 |
| 12 | $4-CH_3$ | — | H | 0 | 0 | 100 | 100 | 100 |
| 13 | $4-CH_3S$ | — | $CH_3$ | 0 | 50(0) | 25 | 0 | 100 |
| 14 | $4-CH_3S$ | — | H | 50 | 100(0) | 50 | 0 | 8 |
| 15 | $4-CH_3S$ | — | $CONHC_6H_4Cl$ | 50 | 100(0) | 0 | 0 | 100 |
| 16 | 4-Br | — | H | 0 | 100(0) | 75 | 0 | 100 |
| 17 | $4-NO_2$ | — | H | 0 | 100(0) | 90 | 0 | 100 |
| 18 | 4-Br | — | $CONHC_6H_4Cl$ | 0 | 100(0) | 50 | 60 | 100 |
| 19 | $2,4-CH_3$ | — | H | 0 | 100(0) | 50 | 0 | 97 |
| 20 | $2,4-CH_3$ | — | $CONHC_6H_4Cl$ | 0 | 100(0) | 0 | 0 | 100 |
| 21 | $2,4-CH_3$ | — | $CON(CH_3)_2$ | 0 | 100(0) | 25 | 0 | 100 |
| 22 | $2-C_6H_5CH_2O$ | — | H | 0 | 80(0) | 95 | 55 | 100 |
| 23 | 2-Cl | — | $CONHC_6H_4Cl$ | 0 | 100(0) | 0 | 0 | 6 |
| 24 | 2-Cl | — | H | 0 | 100(0) | 50 | 10 | 100 |
| 25 | $4-CF_3$ | — | H | 0 | 100(0) | 0 | 100 | 100 |
| 26 | $4-CF_3$ | — | $CONHC_6H_4Cl$ | 0 | 100(0) | 0 | 100 | 100 |
| 27 | $2-C_6H_5CH_2O$ | — | $CONHC_6H_4Cl$ | 50 | 70(0) | 45 | 32 | 48 |
| 28 | $2,4-CH_3$ | — | $CH_3$ | 0 | 70(0) | 25 | 20 | 99 |
| 29 | 2,4-Cl | — | H | 100 | 100(0) | 100 | 20 | 100 |
| 30 | $2-CH_3$ | — | H | 0 | 70(0) | 90 | 0 | 98 |
| 31 | 2,4-Cl | — | $CONHC_6H_4Cl$ | 0 | 0 | 100 | 0 | 100 |
| 32 | 3-Br | — | H | 50 | 100(0) | 100 | 0 | 100 |
| 33 | 3-Br | — | $CONHCH_3$ | 50 | 100(0) | 100 | 40 | 100 |
| 34 | $2-C_6H_5O$ | — | H | 0 | 50(0) | 100 | 0 | 39 |
| 35 | $4-C_2H_5O$ | — | H | 0 | 80(0) | 95 | 0 | 100 |
| 36 | $3-CH_3O$ | — | H | 0 | 100(0) | 100 | 20 | 100 |
| 37 | $4-C_6H_5$ | — | H | 0 | 85(0) | 100 | 80 | 100 |
| 38 | $2-CH_3O$ | — | H | 0 | 70(0) | 60 | 0 | 0 |
| 39 | $3,4-CH_3O$ | — | H | 0 | 50(0) | 95 | 0 | 11 |
| 40 | $4-N(CH_3)_2$ | — | H | 0 | 100(0) | 95 | 0 | 100 |
| 41 | $4-C(CH_3)_3$ | — | H | 0 | 50(0) | 90 | 0 | 98 |
| 42 | $3-CH_3$ | — | H | 0 | 100(0) | 100 | 40 | 98 |
| 43 | $3,4-CH_3O$ | $CH_3$ | H | 0 | 50(0) | 60 | 0 | 1 |
| 44 | 3-F | — | H | 0 | 100(0) | 75 | 20 | 100 |
| 45 | 2-Cl, $4-NO_2$ | — | H | 0 | 100(0) | 100 | 0 | 100 |
| 46 | $2-CH_3$, 4-Cl | $CH_2O$ | H | 0 | 100(0) | 99 | 20 | 100 |
| 47 | 4-F | $CH_2O$ | H | 0 | 100(0) | 100 | 60 | 100 |
| 48 | $4-CH_3O$ | $(CH_2)_2$ | H | 0 | 100(0) | 30 | 0 | 95 |
| 49 | H | $(CH_2)_2$ | H | 0 | 100(0) | 50 | 0 | 100 |
| 50 | 4-Cl | $CH_2O$ | H | 0 | 100(0) | 95 | 4 | 93 |
| 51 | H | $CH_2O$ | H | 0 | 70(0) | 90 | 0 | 100 |

TABLE II

| CMPD # | R³ | R² | MI | MIOVL | RPH | TB | TBOV |
|---|---|---|---|---|---|---|---|
| 52 | $C_4H_3O$ | $CH_3$ | 0 | 0 | 85 | 0 | 0 |
| 53 | $CH_2-C_{10}H_7$ | $CH_3$ | 0 | 0 | 75 | 0 | 1 |

TABLE II-continued

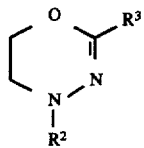

| CMPD # | R³ | R² | MI | MIOVL | RPH | TB | TBOV |
|---|---|---|---|---|---|---|---|
| 54 | $CH_2-C_5H_4N$ | $CH_3$ | 0 | 0 | 75 | 0 | 0 |
| 55 | $CH_2-C_6H_5N$ | H | 0 | 0 | 100 | 0 | 0 |
| 56 | $3-BrC_6H_4$ | H—HCl | 0 | 50(0) | 100 | 0 | 2 |
| 57 | $C_6H_4-N(CH_3)_2$ | H—HCl | 0 | 50(0) | 100 | 0 | 0 |
| 58 | $C_6H_4-4-OC_2H_5$ | H—HCl | 0 | 85(0) | 100 | 0 | 100 |
| 59 | $C_6H_3-2,3-(CH_3O)_2$ | H—HCl | 0 | 80(0) | 95 | 20 | 21 |
| 60 | $C_6H_4-4-C(CH_3)_3$ | H—HCl | 0 | 0 | 95 | 0 | 0 |
| 61 | $C_6H_4-3-CH_3O$ | H—HCl | 0 | 0 | 100 | 0 | 0 |
| 62 | $CH_3$ | H | 0 | 0 | 90 | 0 | 0 |
| 63 | $C_5H_4N$ | H | 0 | 50(0) | 25 | 40 | 0 |
| 64 | $CH_2-C_4H_3S$ | H | 0 | 100(0) | 90 | 0 | 9 |
| 65 | $4-BrC_6H_4$ | H—HCl | 0 | 100(0) | 40 | 40 | 100 |
| 66 | $C_3H_7$ | H | 0 | 0 | 50 | 16 | 7 |
| 67 | $4-BrC_6H_4$ | $CH_2CH_2F$—HCl | 30 | 100(0) | 85 | 100 | 100 |
| 68 | $C_4H_3N_2$ | H | 0 | 100(0) | 70 | 15 | 0 |
| 69 | $4-BrC_6H_4$ | $CONHC_6H_4-4-OCF_3$ | 0 | 0 | 0 | 100 | 5 |
| 70 | $4-BrC_6H_4$ | $CONHC_6H_4-4-CF_3$ | 30 | 0 | 0 | 100 | 1 |
| Comparative Compound A | $4-BrC_6H_4$ | $CH_2CH_2Cl$-HCl | 0 | 0 | 0 | 0 | 0 |

TABLE III

| | |
|---|---|
| 01 | m(2)2.3; m(2)4.5; m(5)7.3–7.8 |
| 02 | m(2)3.0; s(2)3.4; m(2)4.3; s(5)7.3 |
| 03 | m(2)4.0; m(2)4.5; m(9)7.3–8.1; s(1)9.2 |
| 04 | s(3)2.3; m(4)7.1–7.7; s(3)2.9; m(2)3.1; m(2)4.5 |
| 05 | m(2)3.1; s(3)3.8; m(2)4.5; d(2)6.9; d(2)7.7 |
| 06 | m(2)3.1; s(3)3.7; m(2)4.3; m(8)6.9–7.7 |
| 07 | m(2)3.1; m(24.5; m(5)7.2–8.0 |
| 08 | m(2)3.0; m(2)4.2; s(2)4.6; m(4)7.0–7.4 |
| 09 | m(2)3.0; m(2)4.2; s(2)4.6; m(7)7.0–7.5 |
| 10 | m(2)3.2; m(2)4.5; s(2)7.3; S(1)7.5 |
| 11 | m(2)3.2; m(2)4.5; m(5)7.3–7.9 |
| 12 | s(3)2.3, m(2)3.1; m(2)4.5; d(2)7.2; d(2)7.7 |
| 13 | s(3)2.4; s(3)2.8; m(2)3.0; m(2)4.4; m(4)7.1–7.7 |
| 14 | s(3)2.5; m(2)3.2; m(2)4.5; d(2)7.2; d(2)7.6 |
| 15 | s(3)2.5; s(1)8.8; m(2)3.0; m(2)4.4; m(4)7.1–7.7 |
| 16 | m(2)3.1; m(2)4.5; m(5)7.5 |
| 17 | m(2)3.1; m(2)4.5; m(5)8.0 |
| 18 | m(2)3.1; m(2)4.4; m(8)7.0–7.7 |
| 19 | s(3)2.3; s(3)2.4; m(2)3.1; m(2)4.5; m(4)6.8–7.4 |
| 20 | s(3)2.3; s(3)2.4; m(2)3.0; m(2)4.4; m(7)7.0–7.5; s(1)8.7 |
| 21 | s(3)2.3; s(3)2.4; s(6)3.0; m(2)3.0; m(2)4.4; m(3)6.9–7.4 |
| 22 | m(2)3.1; m(2)4.5; s(2)5.0; m(10)6.8–7.5 |
| 23 | m(2)3.0; m(2)4.4; m(8)7.0–7.6 |
| 24 | m(2)3.1; m(2)4.5; m(5)7.1–7.5 |
| 25 | m(2)3.1; m(2)4.5; m(5)7.4–7.9 |
| 26 | m(2)3.1; m(2)4.4; m(8)7.0–7.8 |
| 27 | m(2)3.0; m(2)4.4; s(2)5.0; m(14)7.0–7.5 |
| 28 | s(3)2.3; s(3)2.4; s(3)2.8; m(2)3.0; m(2)4.5 m(3)7.0–7.3 |
| 29 | m(2)3.1; m(2)4.5; m(4)7.1–7.6 |
| 30 | s(3)2.4; m(2)3.1; m(2)4.5; m(5)7.1–7.6 |
| 31 | m(2)4.0; m(2)4.5; m(7)7.1–7.6; s(1)8.5 |
| 32 | m(2)3.1; m(2)4.5; m(4)7.2–7.9 |
| 33 | d(3)2.9; m(2)3.1; m(2)4.4; m(4)7.1–7.9 |
| 34 | m(2)3.0; m(2)4.3; m(9)7.0–7.5 |
| 35 | t(3)1.4; m(2)3.0; q(2)4.0; m(2)4.5; m(2)6.9; m(2)7.8 |
| 36 | m(2)3.0; s(3)3.8; m(2)4.5; m(4)6.9–7.4 |
| 37 | m(2)3.0; m(2)4.5; m(9)7.2–7.9 |
| 38 | m(2)3.0; s(3)3.8; m(2)4.4; m(4)6.9–7.4 |
| 39 | m(2)3.0; s(6)4.0; m(2)4.4; m(3)6.8–7.3 |
| 40 | s(6)3.0; m(2)3.0; m(2)4.4; m(4)6.8–7.8 |
| 41 | s(9)1.3; m(2)3.0; m(2)4.4; m(4)7.4–7.8 |
| 42 | s(3)2.3; m(2)3.1; m(2)4.5; m(4)7.2–7.6 |
| 43 | m(2)3.0; s(2)3.5; s(6)3.9; m(2)4.3; s(3)6.9 |
| 44 | m(2)3.0; m(2)4.4; m(4)7.0–7.6 |
| 45 | m(2)3.1; m(2)4.4; m(3)7.6–8.1 |
| 46 | s(3)2.1; m(2)3.0; m(2)4.3; s(2)4.5; m(3)7.0–7.2 |
| 47 | m(2)3.0; m(2)4.3; s(2)4.4; m(4)6.9–7.1 |
| 48 | m(6)2.7–3.0; s(3)3.7; m(2)4.2–4.4; m(4)6.8–7.2 |
| 49 | m(6)2.5–3.0; m(2)4.1–4.4; s(5)7.2 |
| 50 | m(2)2.8–3.2; m(4)4.2–4.5; m(4)6.8–7.3 |
| 51 | m(2)2.9–3.2; m(4)4.3–4.5; m(5)6.9–7.3 |
| 52 | s(3)2.9; m(2)3.0; m(2)4.5; m(3)6.5–7.4 |
| 53 | s(3)2.7; m(2)3.1; 3(2)4.0; m(2)4.3; m(7)7.3–8.0 |
| 54 | s(3)2.8; m(2)2.9; s(2)3.7; m(2)4.3; m(5)7.0–7.3 |
| 55 | m(2)2.9; s(2)3.8; m(2)4.3; m(5)7.0–7.3 |
| 57 | s(6)3.1; m(2)3.1; m(2)4.4; m(4)7.0–7.5 |
| 58 | t(3)1.4; m(2)3.0; q(2)4.0; m(2)4.3; m(4)6.8–7.9 |
| 59 | m(2)3.0; S(6)4.0; m(2)4.5; m(3)6.9–7.5 |
| 60 | s(9)1.3; m(2)3.1; m(2)4.4; m(4)7.2–7.9 |
| 61 | m(2)3.1; s(3)3.9; m(2)4.4; m(4)7.1–7.7 |
| 62 | s(3)2.0; m(2)3.0; m(2)4.2 |
| 63 | m(2)3.0; m(2)4.5; m(5)7.1–8.8 |
| 64 | m(2)2.9; s(2)3.4; m(2)4.3; m(3)7.0–7.3 |
| 65 | m(2)3.5; m(2)4.6; s(4)7.7 |
| 66 | t(3)1.0; m(2)1.4–1.7; m(2)2.0–2.3; m(2)2.9–3.2; m(2)4.2–4.5 |
| 67 | m(4)3.3–3.9; m(4)4.5–5.5; m(4)7.5–7.9 |
| 68 | m(2)3.1–3.3; m(2)4.5–4.7; s(2)8.5; s(1)9.1 |
| 69 | m(2)3.7–4.0; m(2)4.4–4.7; m(8)7.2–8.2; s(1)9.4 |
| 70 | m(2)3.7–4.0; m(2)4.4–4.7; m(8)7.6–8.2; s(1)9.5 |
| A | m(4)7.6–8.0; t(2)4.5; m(4)3.8–4.1; t(2)3.3 |

EXAMPLE 2

Preparation of Formulations

The remaining examples relate to the pesticidal use of the compounds of this invention. In all these examples a stock solution for the compounds were prepared at 3000 ppm by dissolving 0.3 gram of the compound to be tested in 10 ml of acetone and adding 90 ml of distilled water plus four drops of ethoxylated sorbitan monolaurate, or a simliar suitable wetting agent. For each example that follows, this stock solution was used and the specificied dilutions made.

All the tests discussed below, which involved treatment with compounds of this invention at concentrations of 3000 to 500 ppm were always repeated with controls, in which the active compound was not provided, to permit a comparison upon which the percent control was calculated.

EXAMPLE 3

Mite Adulticide and Mite Ovicide/Larvicide Tests

One day before treatment, a "Figure 8" configuartion of tree tanglefoot was applied to each of two cowpea primary leaves, one from each of two plants in a pot. In each figure, the circle nearer the stem was designated for the mite ovicide/larvicide test and the circle further from the stem was designated for the mite adulticide test.

Groups of adult mites (*Tetranychus urticae* Koch) were transferred into ovicide circles one day before treatment and the females were allowed to deposit eggs until one hour before treatment when the adults were removed. Plants were sprayed to run off with a 1000 ppm solution diluted from the 3000 ppm stock solution.

One day following treatment, groups of approximately 25 adult mites were transferred into the adulticide rings. Five days later these rings were examined for live mites remaining on the leaves. The percent control was estimated based on the number of mites surviving on the check plants.

Nine days following treatment the ovicide/larvicide rings were examined for hatched eggs and living immature mites. The percent control was estimated based on the number of eggs hatching and immature mites surviving on the check plants. When the treatment effect was to eggs, control was designated as ovicidal (O); when the treatment effect was to immatures, control was designated as larvicidal (L).

Results of the mite adulticide (MI) and ovicide/larvicide (MIOVL) tests are presented in Tables I and II.

EXAMPLE 4

Rice Planthopper Foliar Test

The stock solution of 3000 ppm was diluted to 1000 ppm. One pot containing approximately 20 Mars variety rice seedlings was treated with each formulation by spraying with a spray atomizer. One day after treatment plants were covered with a tubular cage and twenty adult rice delphacides, *Sogatodes orizicola*, were transferred into each cage. Five days after transferring, counts were made of the surviving planthoppers in each pot and percent control was estimated.

Results of the testing of rice planthoppers (RPH) are presented in Tables I and II.

EXAMPLE 5

Tobacco Budworm Test

The stock solution of 3000 ppm was used for this test. For each compound, 0.2 ml was pipetted onto the surface of each of 5 diet cells, allowed to spread over the surfaces and air dried for two hours. Then a second instar *Helicoverpa virescens* larva was introduced into each cell. After 14 days, the number of living larvae was determined for each treatment and percent control, corrected by Abbott's formula, was calculated.

The results of the testing of tobacco budworms (TB) are given in Tables I and II.

EXAMPLE 6

Tobacco Budworm Ovicide Test

A solution of 1000 ppm was prepared by dissolving 0.015 g of the compound to be tested in 2 ml of acetone and adding 13 ml of distilled water plus 1 drop of ethoxylated sorbitan monolaurate. Cheesecloth on which budworms had oviposited eggs 1–2 days before treatment was cut into pieces, each containing 40–80 eggs. These pieces were immersed for 1 minute in the solution. After 5 days, the numbers of hatched and unhatched eggs were counted and an adjusted percent control determined. The results are given in Tables I and II.

EXAMPLE 7

Aphid Tests

A solution of 500 ppm was applied by foliar spray to infested host plants, and an estimated percent control was determined at 5 days after treatment. Either green peach aphid (GPA) on tomato or corn leaf aphid (CLA) on barley was evaluated. The results are given below:

TABLE IV

APHID TESTS

| Compound No. | Percent Control | |
| --- | --- | --- |
| | GPA | CLA |
| 5 | 100 | |
| 7 | 100 | |
| 10 | 100 | |
| 11 | | 100 |
| 12 | 95 | |
| 17 | 98 | |
| 19 | | 100 |
| 22 | 99 | |
| 24 | | 100 |
| 25 | | 99 |
| 30 | | 100 |

The test results demonstrate surprising and unexpected efficacy of the compounds of the instant invention as mite adulticides and mite ovicide/larvicides. The compositions were also potent in the control of insect pests including but not limited to rice planthoppers, tobacco budworms, and aphids.

It is apparent that various modifications may be made in the formulation and application of the compounds of this invention without departing from the inventive concepts as defined in the following claims.

What is claimed is:

1. A compound having the formula $$\begin{array}{c} O \quad Z \\ \diagdown \! \! \diagup \\ \| \\ \diagup N \\ N \\ | \\ R^1 \end{array}$$

wherein:

Z is a)

$$-(CH_2)_x-\!\!\left\langle\!\!\bigcirc\!\!\right\rangle\!\!-R_n$$

wherein x is an integer from 0 to 4, n is an integer from 0 to 5 and R is defined below; or b)

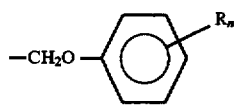

wherein n is an integer from 0 to 5 and R is defined below;

R is selected from the group consisting of: hydrogen; $C_1$–$C_4$ alkyl; $C_1$–$C_4$ alkoxy; halogen; nitro; phenyl; cyano; phenoxy; benzyloxy; benzyl; $C_1$–$C_4$ dialkylamino; $C_1$–$C_4$ alkylthio; or $C_1$–$C_4$ haloalkyl; and $R^1$ is a $C_1$–$C_4$ fluoroalkyl;

or physiologically acceptable salts thereof.

2. A compound as recited in claim 1 wherein Z is option a); n is 1 or 2; and x is 0.

3. A compound as recited in claim 2 wherein R is hydrogen, $C_1$–$C_4$ alkyl, $C_1$–$C_4$ alkoxy, halogen or $C_1$–$C_4$ alkylthio.

4. An insecticidal or acaricidal composition comprising:
(A) an effective amount of a compound as recited in claim 1; and
(B) a suitable carrier.

5. An insecticidal or acaricidal composition comprising:
(A) an effective amount of a compound as recited in claim 2; and
(B) a suitable carrier.

6. An insecticidal or acaricidal composition comprising:
(A) an effective amount of a compound as recited in claim 3; and
(B) a suitable carrier.

7. A method for controlling insects or acarids which comprises applying to a locus to be protected an effective amount of a compound as recited in claim 1.

8. A method for controlling insects or acarids which comprises applying to a locus to be protected an effective amount of a compound as recited in claim 2.

9. A method for controlling insects or acarids which comprises applying to a locus to be protected an effective amount of a compound as recited in claim 3.

\* \* \* \* \*